(12) United States Patent
Panhans et al.

(10) Patent No.: US 12,401,104 B2
(45) Date of Patent: Aug. 26, 2025

(54) ROTARY TRANSMISSION SYSTEM USING A WAVEGUIDE

(71) Applicant: Schleifring GmbH, Fürstenfeldbruck (DE)

(72) Inventors: Christian Panhans, Augsburg (DE); Reinhard Stolle, Aresing (DE)

(73) Assignee: Schleifring GmbH, Fürstenfeldbruck (DE)

( * ) Notice: Subject to any disclaimer, the term of this patent is extended or adjusted under 35 U.S.C. 154(b) by 315 days.

(21) Appl. No.: 18/179,679

(22) Filed: Mar. 7, 2023

(65) Prior Publication Data
US 2023/0207997 A1    Jun. 29, 2023

Related U.S. Application Data

(63) Continuation of application No. PCT/EP2021/074111, filed on Sep. 1, 2021.

(30) Foreign Application Priority Data

Sep. 8, 2020 (EP) .................................... 20195123
May 3, 2021 (EP) .................................... 21171782

(51) Int. Cl.
  *H01P 1/06* (2006.01)
  *A61B 6/42* (2024.01)
(52) U.S. Cl.
  CPC ............ *H01P 1/062* (2013.01); *A61B 6/4208* (2013.01)
(58) Field of Classification Search
  CPC ........ H01P 1/062; H01P 1/068; A61B 6/4208; A61B 6/035; A61B 6/56
  See application file for complete search history.

(56) References Cited

U.S. PATENT DOCUMENTS

| | | | |
|---|---|---|---|
| 2,945,193 A | 7/1960 | Strom | |
| 5,530,422 A * | 6/1996 | Harrison | ............... G01N 23/046 378/4 |
| 5,600,697 A * | 2/1997 | Harrison | .................. A61B 6/56 378/19 |
| 5,646,962 A | 7/1997 | Harrison | |

(Continued)

FOREIGN PATENT DOCUMENTS

EP    0093468 A1    11/1983

OTHER PUBLICATIONS

Sophocles, Chapter 9—Waveguides, In "Electromagnetic Waves and Antennas", Aug. 2016, vol. 10111113, pp. 362-410.

(Continued)

*Primary Examiner* — John W Poos
(74) *Attorney, Agent, or Firm* — Quarles & Brady LLP; Yakov Sidorin (57) ABSTRACT

A coupler provides a high speed datalink between rotating parts and comprises a circular channel, enclosing a hollow-cylindric volume, and at least two antennas. The circular channel is made of electrically conductive material and includes an inner ring, an outer ring rotatable against the inner ring, and two sidewalls on the sides of the rings. An inner antenna is mechanically coupled to the inner ring and an outer antenna is mechanically coupled to the outer ring. The antennas are configured to establish a microwave signal connection between them based on multiple reflections of an electromagnetic wave at the rings.

20 Claims, 4 Drawing Sheets

(56) References Cited

U.S. PATENT DOCUMENTS

| | | | |
|---|---|---|---|
| 9,968,328 B2 * | 5/2018 | Murray | H01F 38/18 |
| 2007/0063785 A1 * | 3/2007 | Krumme | A61B 6/56 |
| | | | 333/24 R |
| 2016/0235387 A1 | 8/2016 | Murray | |
| 2017/0332991 A1 * | 11/2017 | Fackelmeier | A61B 6/56 |
| 2019/0020121 A1 | 1/2019 | Paulotto et al. | |
| 2019/0274578 A1 | 9/2019 | Semenov et al. | |
| 2020/0194861 A1 | 6/2020 | Vynohradov et al. | |
| 2020/0212528 A1 | 7/2020 | Milroy et al. | |

OTHER PUBLICATIONS

PCT International Search Report and Written Opinion, PCT/EP2021/074111, Nov. 19, 2021, 17 pages.
Song, H. et al., Terahertz Device Technologies for Ultrafast Data Downburst Applications, NTT Technical Review, 2015, 13(1):35-41.
European Patent Office, Extended Search Report, Application No. 21171782.2, Oct. 14, 2021, 10 pages.

* cited by examiner

ROTARY TRANSMISSION SYSTEM USING A WAVEGUIDE

CROSS-REFERENCE TO RELATED APPLICATIONS

This application is a continuation of pending International Application No. PCT/EP2021/074111 filed on Sep. 1, 2021, which designates the United States and claims priority from the European Application No. 20195123.3 filed on Sep. 8, 2020, and the European Application No. 21171782.2 filed on May 3, 2021. The disclosure of each of the above-identified applications is incorporated by reference herein.

BACKGROUND

1. Field of the Invention

The invention relates to a rotary transmission system for providing a non-contact high speed datalink between rotating devices and which may specifically be used for computed tomography scanners.

2. Description of the Related Art

Non-contact data links may be used to couple rotating devices like the rotating part of the gantry of a computed tomography (CT) scanner to the stationary part. Data rates are in the above 1 Gbit/s or even more than 10 Gbit/s range. Such data links may also be called a rotary joint or a slipring.

As CT scanners have a large inner bore for accommodation of a patient to be scanned, rotary joints used therein must have a large diameter, which normally is in the 1-1.5 m range. U.S. Pat. No. 5,646,962 discloses such a non-contact rotary joint which is based on a stripline for guiding a signal around a circular body and a capacitive pickup movable thereto for receiving said signal.

Another approach as disclosed in EP 0 093 468 uses a waveguide for transmitting signals. A stationary waveguide, comprising a circular shaped, conductive hollow body has a fixed receiving antenna. Further, a rotatable transmission antenna is movable in a radial slot in the body to couple signals into the interior of the waveguide. These signals travel along the waveguide until they reach the receiving antenna.

A problem is the comparatively small relative bandwidth of the waveguide, which limits the usable data rate. Further, the radial slot in the waveguide must be comparatively narrow to avoid degradation of the waveguide. The transmission antenna must fit into this slot and therefore can only be a small pin. Such an antenna is limited in its bandwidth and efficiency.

SUMMARY OF THE INVENTION

The embodiments provide an improved high-speed coupling between rotatable parts.

A rotary joint which includes a high speed data link between rotatable parts comprises a circular channel. The circular channel may include an inner ring and an outer ring. Both rings are rotatable relative to each other around an axis which may be the rotation axis of the rotary joint. The outer ring has a larger diameter than the inner ring, thereby providing a radial gap or a space between the rings. Further, the inner ring and the outer ring may be aligned axially. Basically, any of the rings may be stationary, whereas the other is rotatable.

The circular channel further may include at least one or two sidewalls. A first sidewall is located axially on one side of the rings, whereas the second sidewall is located axially on the other or opposing side of the rings. The inner ring, the outer ring, the first sidewall and the second sidewall form a circular channel which may have a rectangular or square cross-section. Basically, any of the sidewalls may be stationary, or rotatable.

The sidewalls are not necessary for the transmission function of the channel but can help to decouple the signal transmitted from the environment or neighboring channels by using reflective or absorptive sidewalls. Thus, also a standard wireless bus as e.g. IEEE 802.11 can be used without interfering with external wireless bus installations used for other purposes.

For transmitting signals, an inner antenna is mechanically coupled to the inner ring and an outer antenna is mechanically coupled to the outer ring. The inner antenna and the outer antenna are directed into a space between the inner ring and the outer ring. This allows to transfer microwave signals between the inner antenna and the outer antenna, if one of the antennas radiates signals into the channel and the other antenna receives signals from the channel. The channel and specifically the inner ring and the outer ring may reflect microwave signals, such that the microwave signals propagate through the ring. To improve reflection of the signals, the channel and specifically the rings and/or the sidewalls may include an electrically conductive material, which may be a metal. They may be made of such a conductive material, or they may have a surface coated with such a conductive material.

The rings (210, 220) and/or sidewalls (230, 240) may be of an electromagnetically reflective material e.g. conductive material or have a conductive surface or are of a dielectric material with high permittivity.

Such a rotary joint may be used in a gantry of a CT scanner which includes a stationary part and a rotating disk, which rotates about a rotation axis. The rotating disk may hold components like a power supply, an X-ray tube, an X-ray detector, and a data acquisition system. The rotary joint may receive data from the data acquisition system and couple these to the stationary part.

The channel may have a rectangular or square cross-section. Therefore, it may be described as a hollow rectangular or square toroid. Normally, the channel may be a void space, filled with air, but it may also include a dielectric material, which may at least partially fill the channel.

In an embodiment, the inner ring may be mounted and/or connected to the first sidewall, and the outer ring may be mounted and/or connected to the second sidewall, thus for. This results in two parts which are rotatable against each other. There may be two gaps between these two parts which may be very close or which may be bridged by sliding contacts, springs, a gasket or any other means which may provide low electrical impedance between these two parts, which may be a capacitive overlap. This improves shielding and avoids unwanted radiation. It is basically the same, if the inner ring is mounted and/or connected to the second sidewall and the outer ring is mounted and/or connected to the first sidewall.

In an embodiment, the inner ring may be mounted to the first sidewall and to the second sidewall, such that the inner ring is rotatable together with the first and second sidewalls. To allow a rotation, a gap may be provided on both sides of the outer ring, such that the outer ring can move freely against the inner ring and the sidewalls. An inverted embodiment may include an outer ring mounted to the first sidewall and the second sidewall.

Basically, there may be any combination of parts connected, as long as the inner ring is rotatable against the outer ring. Any gap between rotatable parts may be bridged by sliding contacts, springs, a gasket or any other means which may provide low electrical impedance between these two parts, which may be a capacitive overlap. The gap may have a width of 0.5 to 4 mm, which may be just big enough to allow rotation and mechanical tolerances of objects of that size.

In an embodiment, the inner ring and the outer ring may have the same width and are axially aligned. Further, the first sidewall and the second sidewall may be flat disk-shaped rings covering the space between the inner ring and the outer ring. At least one of the sidewalls may overlap at least one the rings to bridge a gap there-between and to provide at least a capacitive coupling. The overlap might be dimensioned to be a quarter or multiple quarters of the wavelength.

In an embodiment, the distance between the inner ring and the outer ring is close to five times the wavelength. The distance may be five times the wavelength with a tolerance of plus or minus 50%. This may allow for lowest dispersion between the signal paths with lowest and highest number of reflections.

In an embodiment, the inner antenna and/or the outer antenna have an adjustable directivity wherein transmitted power and receiver sensitivity together with conductivity of the reflective surface of inner and outer ring may be configured for a predetermined number of reflections between the rings leading to a sufficiently low signal after one round of propagation.

In an embodiment, the inner antenna and/or the outer antenna are directed into the circular channel. If a microwave signal is radiated into the channel, it will be reflected by the channel, such that it can be received from the channel. Therefore, in general the embodiments may work with unspecific antennas simply radiating into the channel and receiving from the channel. Improved transmission may be achieved by directing the inner antenna towards the outer ring and the outer antenna towards the inner ring. This ensures proper reflection by the rings to transfer the signals. In a further embodiment, the antennas may have a configurable directivity. This means that they have an adjustable radiation pattern. This may simply be achieved by phased array antennas. The radiation pattern may be adjusted such that a specific angle of reflection is obtained which may result in a well-defined signal path between the inner antenna and the outer antenna. There may also be different or multiple signal paths which may further be used for multiple channels. This may increase transmission rate and/or transmission quality. In an example, there may be a first signal path having two reflections, and another signal path having three reflections. These may be well separated due to their different reflection angles by selective antennas. There may be any number of signal paths.

Another embodiment relates to a data link between movable parts comprising a hollow channel in general. This hollow channel may have a linear shape, but it may also have any other shape like a combination of linear and/or curved sections. The hollow channel may include four sidewalls which may define a rectangular or squared cross-section. This embodiment is comparable to the circular channel embodiments disclosed herein. The linear hollow channel may include a first sidewall with a first antenna, and a second sidewall opposing thereto with a second antenna. The first and second sidewalls may be parallel to each other to allow reflections between the first and second sidewalls. There may be third and fourth sidewalls at the sides of the first and second sidewalls to form the hollow channel.

The circular channel may have a height and a width. Also, the linear hollow channel may have a height and a width. The channel can only guide microwave signals if a wavelength of the microwave signal is shorter than 2 times the width or the height, whichever is larger. The embodiments work best, if at least one wavelength of the microwave signals, which may have multiple different wavelengths, is shorter than ½, ⅓, ¼, ⅕, or ⅒, or 1/20 or 1/50, or 1/100 of the width or the height, whichever is larger. The smaller the wavelength of the signal is compared to the width or to the height of the channel, the more transmission paths under different angles are possible. As the main transmission may be reflection between the inner and the outer ring, or between the first and second sidewalls, at least one wavelength of the microwave signal may be shorter than ½, ⅓, 14, ⅕, or ⅒, or 1/20 or 1/50, or 1/100 of this distance.

The distance between the inner ring and the outer ring may be significantly larger than half of a wavelength of the transmitted signal to allow for a multimode propagation of the signal.

Herein, the term microwave is used for radiofrequency signals which are in a range of more than 300 MHz. In an embodiment, signals in a range above 2 GHz may be used. Very good transmission characteristics have been obtained with signals in a 60 GHz range. The embodiments may also use frequencies of several 100 GHz or more.

In an embodiment, the data transmission implemented may conform to a wireless standard e.g. IEEE802.11 ad or ay.

The dimensions of inner and outer ring may be optimized to achieve a typical number of reflections when the microwave signal is propagating one round. The strategy to optimize the angle is to find an angle where the antenna has a defined directivity, resulting in a transmitted narrow beam of high amplitude with a strong attenuation outside the beam and few side lobes. The same directivity profile may be present at the receive side. Also, the angle may not be as steep, such that the reflections at the opposing ring go back into the antenna. This may be achieved with a two-dimensional patch antenna as phased array antenna with sufficient angular resolution.

Also, the reflection attenuation defined by conductivity and angle of reflection may be optimized, a higher conductivity of the material leads to a lower attenuation, a lower conductivity to a higher attenuation. The strategy is to reduce dispersion (delay spread) between signals having a different number of reflections because of the higher attenuation caused with every reflection.

One angle of reflection is preferred by the directivity characteristic of the main beam of the antenna and side lobes may be present but experience a higher reflection attenuation that additionally attenuates these paths so that the majority of the signal paths varies only slightly in regard to its total path lengths and angles.

Axial displacement of transmitter and receiver may reduce the dynamic range of received signal strengths between minimum signal path 0 degrees and signal path 360 degrees.

Attenuating material may be mounted to at least one of the rings axially to the antenna and in the vicinity of the antenna to attenuate a part of the signal that propagates more than a full round, reducing the interference of directly received signal and signal that propagates more than one round.

An embodiment may use a feature of the wireless standards as e.g. IEEE802.11 ad or ay: the guard interval together with OFDM or single carrier with frequency domain equalization. The transceiver may periodically train on the characteristics of the channel, multiple transmission paths like clockwise and counterclockwise transmission can be employed. A guard interval of the standard applied may be selected such that it is shorter than the signal propagation time through the channel. For a given guard interval, the distance between the inner ring and the outer ring may be adapted to obtain a predetermined maximum path length resulting in a predetermined maximum signal propagation time.

Guard intervals of the above-mentioned wireless standards may be used to allow for multi-path propagation. There may be a training to optimize the guard intervals.

There might be several parallel channels arranged radially or axially. The axial arrangement is preferred with multiple antennas coupled having sidewalls to separate channels. Thus, the total transmission capacity can be increased when there is sufficient attenuation between the channels.

The transmit and receive frequencies might be different at a transceiver to have a better signal separation between the communication channels.

BRIEF DESCRIPTION OF DRAWINGS

In the following the invention will be described by way of example, without limitation of the general inventive concept, on examples of embodiment with reference to the drawings.

Generally, the drawings are not to scale. Like elements and components are referred to by like labels and numerals. For the simplicity of illustrations, not all elements and components depicted and labeled in one drawing are necessarily labels in another drawing even if these elements and components appear in such other drawing.

While various modifications and alternative forms, of implementation of the idea of the invention are within the scope of the invention, specific embodiments thereof are shown by way of example in the drawings and are described below in detail. It should be understood, however, that the drawings and related detailed description are not intended to limit the implementation of the idea of the invention to the particular form disclosed in this application, but on the contrary, the intention is to cover all modifications, equivalents and alternatives falling within the spirit and scope of the present invention as defined by the appended claims.

DETAILED DESCRIPTION

Figure 1:
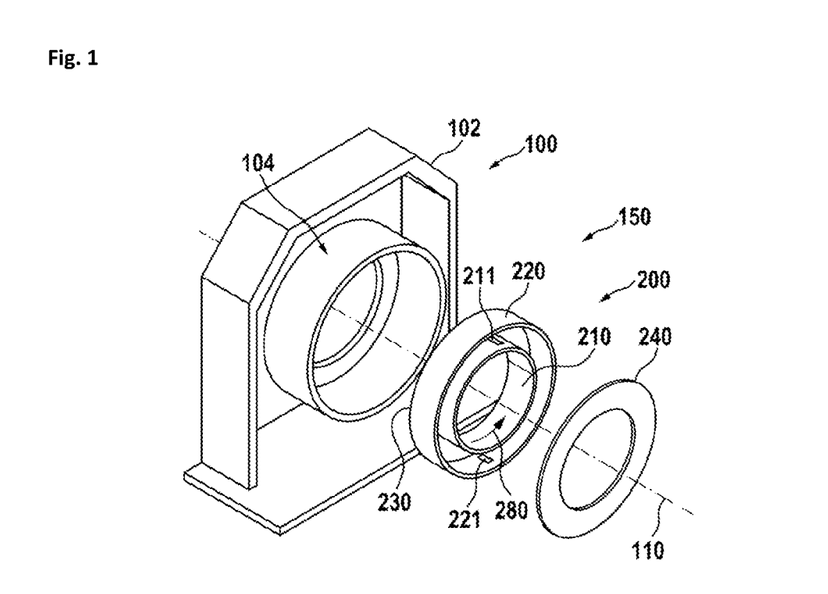
FIG. 1 shows an embodiment.

In FIG. 1 a first embodiment is shown. A gantry 100 of a CT scanner comprises a stationary part 102 and a rotating disk 104, rotating about a rotation axis 110. The rotating disk may hold rotating components which are not shown here, like a power supply, an X-ray tube, an X-ray detector and a data acquisition system. Further, a slip ring or a rotating power transformer which is also not shown, may be provided for transfer of power from the stationary to the rotating part.

A rotary joint 150 for high speed data transmission includes a circular shaped channel 200. It may be described as a hollow rectangular or square toroid. The channel 200 encloses a hollow-cylindric volume. The channel 200 may include an inner ring 210 and an outer ring 220, both rings may be on the same axis. The embodiment would also work with offset axes. Both rings are rotatable against each other. Any one of the rings may be stationary, whereas the other may be rotatable.

To form a channel 200, a first sidewall 230 and/or a second sidewall 240 may be provided. Also, at least one of the sidewalls may be part of a gantry 100 of a CT scanner. Each sidewall may be fixed to one of the rings 210, 220. There may also be a low impedance contact between a sidewall and a ring. To the other ring there may be a gap, which may be bridged by sliding brushes, a conductive gasket or any other suitable material which may provide a good electrical contact.

In an embodiment, the ring 210 and both sidewalls 230, 240 may be connected together forming an U-shaped cross section, while ring 220 is rotatable. There may be gaps at the sides of the outer ring 220 to allow for rotation. There may be any other combination of connected parts which may allow rotation of the rings 210 and 220 with their mechanically coupled antennas 211 and 221 and may form a toroid with rectangular section together with sidewalls.

Both rings 210, 220 may have the same length and may be axially aligned. The sidewalls 230, 240 may be flat disk shaped rings, they may also overlap at least one of the inner ring 210 and the outer ring 220.

The rings 210, 220 and the sidewalls 239, 240 comprise an electrically conductive material like a metal and or a material with electrically conductive surfaces.

An inner antenna 211 is at the inner ring 210 while an outer antenna 221 is at the outer ring 220. The antennas may rotate or be stationary with their rings, the antennas being mounted to the rings.

Figure 2:
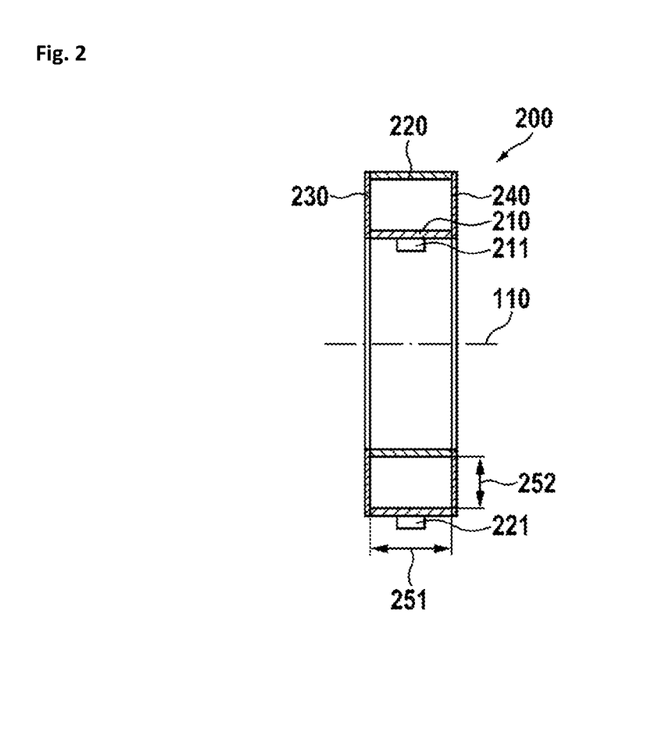
FIG. 2 shows a sectional side view of the circular channel.

FIG. 2 shows a sectional side view of the circular channel 200. The channel may have a rectangular or squared cross section with a width 251 between the sidewalls 230, 240 and a height 252 between the rings 210, 220.

The waveguide has an inner space which allows the propagation of electromagnetic waves with a maximum wavelength $\lambda k$ equals to two times the width 251 or the height 252, whichever is larger.

Since the sidewalls 230, 240 are not necessary for the function they can be omitted, then the width of the channel may be the smallest width of the rings 210, 220.

Figure 3:
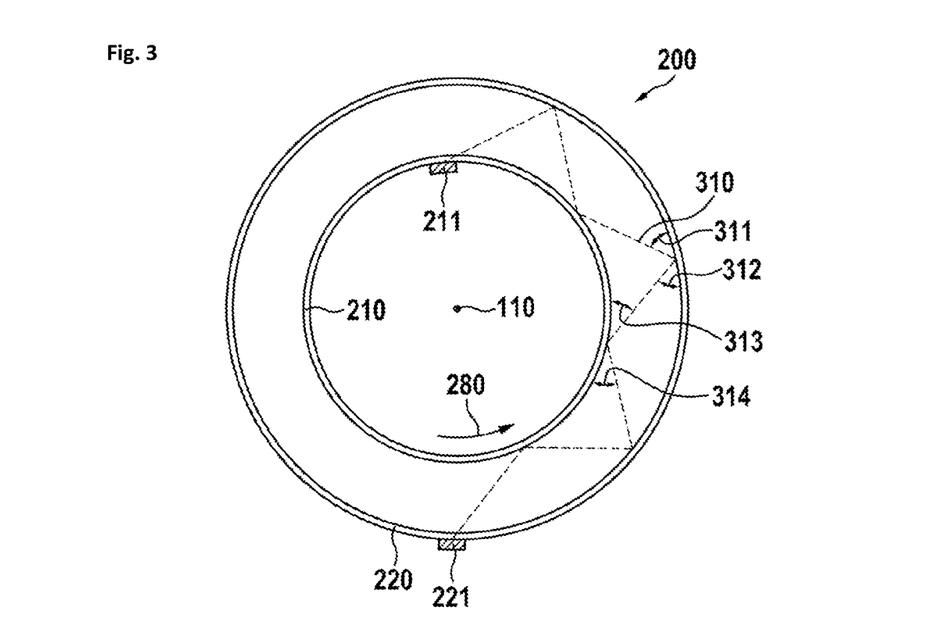
FIG. 3 shows a front view into the circular channel.

FIG. 3 shows a front view into the circular channel 200 with a possible signal path between inner antenna 211 and outer antenna 221. The signal may not only be transmitted in a single mode within the circular channel 200, but it may also be reflected at the inner ring 210 and or the outer ring 220. In this figure, inner antenna 211 and outer antenna 221 have a relative angle of about 180 degrees. There may be multiple reflections at the rings as shown and dependent of the specific direction of radiation of the antennas. With each reflection the angles of the electromagnetic wave 310 to be reflected and the reflected wave versus a surface of a ring are the same. Such, the first angle at outer ring 311 is the same as the second angle at outer ring 312 and the first angle at inner ring 313 is the same as second angle at inner ring 314.

Figure 4:
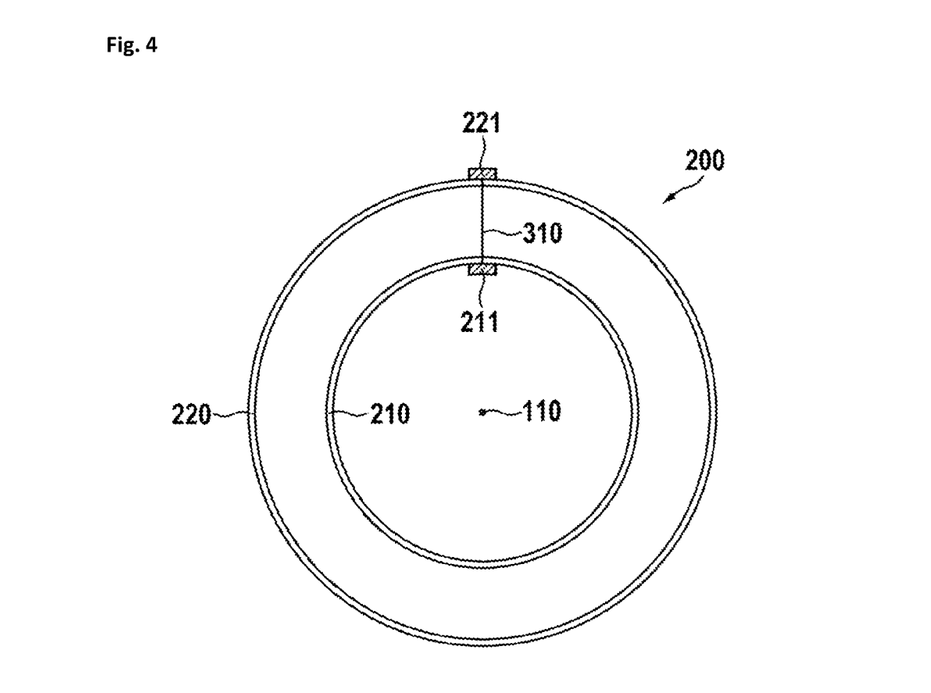
FIG. 4 shows a further front view into the circular channel.

FIG. 4 shows a further front view into the circular channel 200. In this figure, inner antenna 211 and outer antenna 221 have a relative angle of about 0 degrees, such that they are opposing each other. Here, the electromagnetic wave 310 may directly propagate from inner antenna 211 to outer antenna 221.

Figure 5:
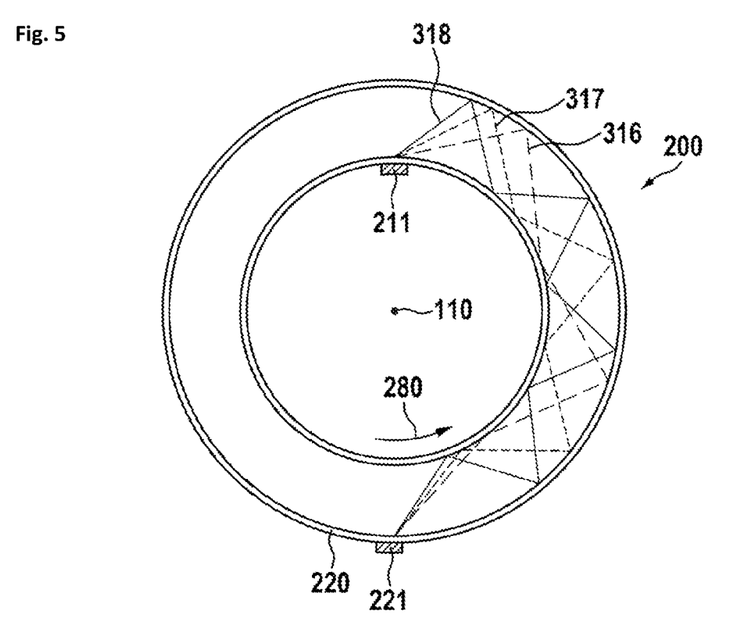
FIG. 5 shows a dual path propagation.

FIG. 5 shows a dual path propagation. In this figure, inner antenna 211 and outer antenna 221 have a relative angle of about 270 degrees. Here, the electromagnetic wave 310 may propagate clockwise from inner antenna 211 to outer antenna 221. There may also be a second counterclockwise signal path 315, if the antennas are set to radiate accordingly. The antennas and/or transmitter and/or receiver may switch between these signal paths to select the best one. Both signal paths may also be used to increase date rate. Further, both signal paths may be used for bidirectional signal transmission. This example shows a relative angle of about 270 degrees, but two signal paths are basically available through all relative angles between inner antenna 211 and outer antenna 221.

Figure 6:
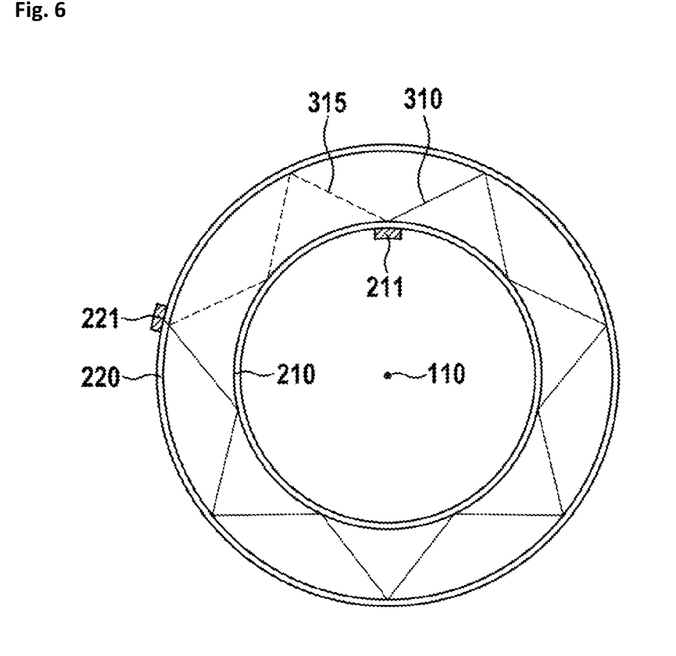
FIG. 6 shows a multipath propagation.

FIG. 6 shows a multipath propagation. In this figure, inner antenna 211 and outer antenna 221 have a relative angle of about 180 degrees. Here three different multipath propagations 316, 317, 318 are shown. This may be used to further increase bandwidth.

Figure 7:
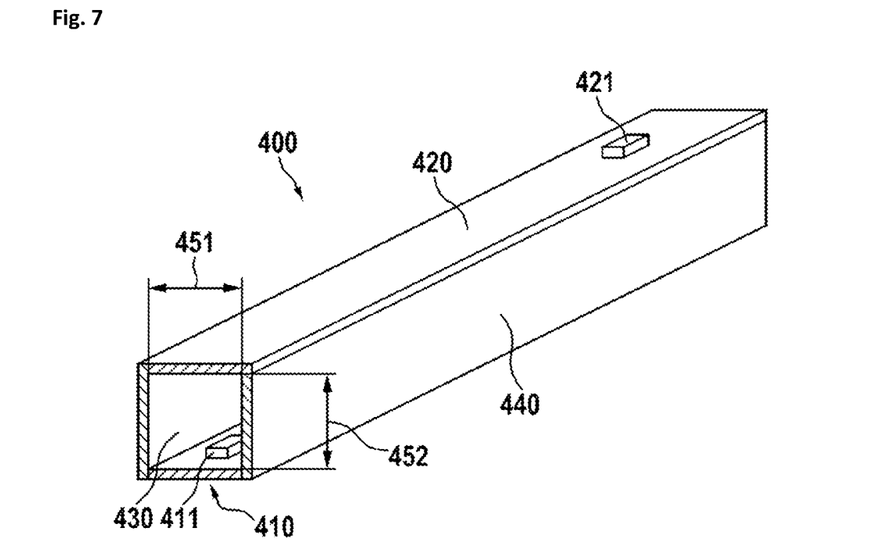
FIG. 7 shows a linear embodiment.

FIG. 7 shows a linear embodiment. A hollow channel 400 includes four sidewalls 410, 420, 430, 440, defining a rectangular cross sectioned or square cross sectioned hollow space. A first sidewall 410 is parallel to a second sidewall 420. Further, a first antenna 411 is mechanically coupled to the first sidewall 410 and a second antenna 421 is movable within the linear channel. The second antenna may be coupled to the second sidewall. The sidewalls 410, 420, 430, 440 include an electrically conductive material like a metal. They may be made from such a material or they may have a conductive surface which may include such a material. The first antenna 411 and the second antenna 421 are configured for a microwave signal connection 169 between them. This embodiment is basically the same as the circular embodiments disclosed herein, but is linear. The first sidewall 410 corresponds to the inner ring 210 and the second sidewall 420 corresponds to the outer ring 220. Further, an embodiment may have any shape like a combination of curved sections and/or linear sections.

Figure 8:
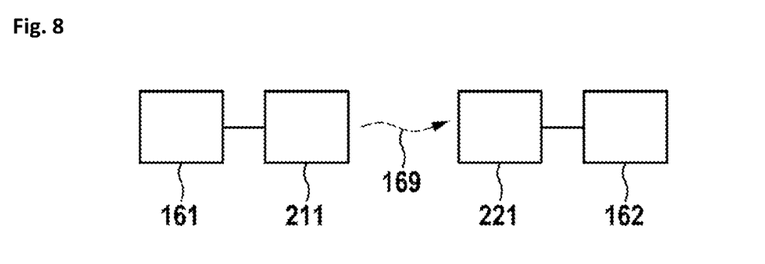
FIG. 8 shows an exemplary functional block diagram.

FIG. 8 shows an exemplary functional block diagram. A transmitter 161, which may be fed by a data acquisition system providing imaging data sends signals to inner antenna 211 which radiates microwave signals 169 into the circular channel 200. These RF signals 169 are received by antenna 221 and for-warded to a receiver 162. Basically, the direction may be reversed. Also a bidirectional communication may be made.

It will be appreciated to those skilled in the art having the benefit of this disclosure that this invention is believed to provide a rotary joint providing a high speed datalink. Further modifications and alternative embodiments of various aspects of the invention will be apparent to those skilled in the art in view of this description. Accordingly, this description is to be construed as illustrative only and is provided for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 100 gantry of CT scanner
102 stationary part
104 rotatable disk
110 rotation axis
150 rotary joint
161 transmitter
162 receiver
169 RF signals
200 circular channel
210 inner ring
211 inner antenna
220 outer ring
221 outer antenna
230 first sidewall
240 second sidewall
251 width
252 height
310 electromagnetic wave propagation
311 first angle at outer ring
312 second angle at outer ring
313 first angle at inner ring
314 second angle at inner ring
315 alternate electromagnetic wave propagation
316 first multipath propagation
317 second multipath propagation
318 third multipath propagation
400 hollow channel
410 first sidewall
420 second sidewall
411 first antenna
420 second sidewall
421 second antenna
430 third sidewall
440 fourth sidewall
451 width
452 height

What is claimed is:

1. A rotary joint providing a high speed datalink between rotatable parts comprising a circular channel,
   wherein the circular channel includes:
   an inner ring and an outer ring,
   both the inner and outer rings being centered about a common rotation axis and being rotatable against each other,
   the outer ring having a larger diameter than that of the inner ring,
   a first sidewall located axially on one side of the inner and outer rings and a second sidewall opposing the first sidewall and located axially on the other side of the inner and outer rings,
   wherein the inner ring is mounted to the first sidewall and
   the outer ring is mounted to the second sidewall,
   an inner antenna mechanically coupled to the inner ring, and
   an outer antenna mechanically coupled to the outer ring;
   wherein the inner antenna and the outer antenna are directed into a space between the inner ring and the outer ring and configured for a microwave signal connection between the inner and outer antennae; and wherein the rotary joint has a first gap between the inner ring and the second sidewall and a second gap between the outer ring and the first sidewall.

2. A rotary joint according to claim 1, wherein:
one of the inner ring and the outer ring is mounted to the first sidewall and the second sidewall, thereby forming a corresponding gap on each side of the other one of the outer ring and the inner ring to the first sidewall and the second sidewall, or
the outer ring is mounted to the first sidewall and the second sidewall, thereby forming a respective gap on each side of the inner ring to the first sidewall and the second sidewall.

3. A rotary joint according to claim 1, wherein at least one of gaps present in the rotary joint is bridged by at least a sliding contact, a gasket, a seal, or an overlap providing capacitive coupling.

4. A rotary joint according to claim 1, wherein the first sidewall and/or the second sidewall is disc shaped and has a center hole.

5. A rotary joint according to claim 1, wherein the circular channel encloses a hollow-cylindric volume.

6. A rotary joint according to claim 1, wherein at least one of the inner and outer rings and/or the first and second sidewalls is made of a conductive material or has a conductive surface or is made of a dielectric material with high permittivity.

7. A rotary joint according to claim 1, wherein a distance between the inner ring and the outer ring is larger than half of a wavelength of a microwave signal.

8. A rotary joint according to claim 1, wherein the inner antenna and/or the outer antenna have an adjustable directivity to configure at least an angle of radiation to a predetermined value or a position-dependent value.

9. A rotary joint according to claim 1, wherein an adjustable directivity of an antenna of the inner and outer antennae is selected to produce a beam that experiences a first reflection at an opposing ring and a second reflection outside the antenna.

10. A rotary joint according to claim 1, wherein the inner antenna and/or the outer antenna has an adjustable directivity and is configured to adapt a transmitted power and a receiver sensitivity dependent on conductivity of a reflective surface of the inner and outer rings such as to have a microwave signal reflect between the inner ring and the outer ring a predetermined number of times.

11. A rotary joint according to claim 1, wherein
a) the inner antenna and the outer antenna are axially displaced with respect to each other and/or
b) the inner ring and/or the outer ring have a microwave signal-attenuating material affixed axially to the inner antenna and the outer antenna and/or
c) the inner antenna and/or the outer antenna are directed into the channel and/or
d) the inner antenna is directed towards the outer ring and/or the outer antenna is directed towards the inner ring.

12. A rotary joint according to claim 2, wherein at least one of gaps present in the rotary joint is bridged by at least a sliding contact, a gasket, a seal, or an overlap providing capacitive coupling.

13. A rotary joint according to claim 1, at least one of the inner and outer rings and/or the first and second sidewalls is made of a conductive material or has a conductive surface or is made of a dielectric material with high permittivity.

14. A rotary joint providing a high speed datalink between rotatable parts comprising a circular channel, wherein the circular channel includes:
an inner ring and an outer ring,
both the inner and outer rings being centered about a common rotation axis and being rotatable against each other,
the outer ring having a larger diameter than that of the inner ring,
an inner antenna mechanically coupled to the inner ring, and
an outer antenna mechanically coupled to the outer ring; wherein
the inner antenna and the outer antenna are directed into a space between the inner ring and the outer ring and configured for a microwave signal connection between the inner and outer antennae;
wherein at least one of the first sidewall and the second sidewall includes a material configured to absorb and/or reflect a microwave signal or includes a combination of a material configured to absorb the microwave signal and a conductive surface, said material configured to absorb the microwave signal being mounted on the conductive surface.

15. A rotary joint according to claim 14, wherein distance between the inner ring and the outer ring is larger than half of a wavelength of a microwave signal.

16. A rotary joint according to claim 14, wherein the inner antenna and/or the outer antenna have an adjustable directivity to configure at least an angle of radiation to a predetermined value or a position-dependent value.

17. A rotary joint according to claim 14, wherein an adjustable directivity of an antenna of the inner and outer antennae is selected to produce a beam that experiences a first reflection at an opposing ring and a second reflection outside the antenna.

18. A rotary joint according to claim 14, wherein
the inner antenna and/or the outer antenna has an adjustable directivity and is configured to adapt a transmitted power and a receiver sensitivity dependent on conductivity of a reflective surface of the inner and outer rings such as to have a microwave signal reflect between the inner ring and the outer ring a predetermined number of times.

19. A rotary joint according to claim 1, wherein
a) the inner antenna and the outer antenna are axially displaced with respect to each other and/or
b) the inner ring and/or the outer ring have a microwave signal-attenuating material affixed axially to the inner antenna and the outer antenna and/or
c) the inner antenna and/or the outer antenna are directed into the channel and/or
d) the inner antenna is directed towards the outer ring and/or the outer antenna is directed towards the inner ring.

20. A rotary joint providing a high speed datalink between rotatable parts comprising a circular channel, wherein the circular channel includes:
an inner ring and an outer ring,
both the inner and outer rings being centered about a common rotation axis and being rotatable against each other,
the outer ring having a larger diameter than that of the inner ring,
an inner antenna mechanically coupled to the inner ring, and
an outer antenna mechanically coupled to the outer ring;

wherein
the inner antenna and the outer antenna are directed into a space between the inner ring and the outer ring and configured for a microwave signal connection between the inner and outer antennae;

wherein the circular channel defines a width between the first and second sidewalls and a height between the inner and outer rings, wherein at least one wavelength of the microwave signal is shorter than two times the larger of the width and the height, and wherein the at least one wavelength of the microwave signal is shorter than $1/3$ and/or $1/5$ and/or $1/10$ and/or $1/20$ and/or $1/50$ and/or $1/100$ of the larger of the width and the height.

* * * * *